United States Patent [19]

Pagano

[11] 4,174,636
[45] * Nov. 20, 1979

[54] TWO WHEEL ULTRASONIC RAIL TESTING SYSTEM AND METHOD

[76] Inventor: Dominick A. Pagano, 10 Sasqua Trail, Georgetown, Conn. 06829

[ * ] Notice: The portion of the term of this patent subsequent to Aug. 28, 1996, has been disclaimed.

[21] Appl. No.: 820,588

[22] Filed: Aug. 1, 1977

Related U.S. Application Data

[63] Continuation-in-part of Ser. No. 818,544, Jul. 25, 1977.

[51] Int. Cl.² .......................................... G01N 29/04
[52] U.S. Cl. .......................................... 73/636; 73/639
[58] Field of Search ................. 73/618, 620, 624, 625, 73/627, 628, 629, 632, 634, 635, 636, 639, 641

[56] References Cited

U.S. PATENT DOCUMENTS

| | | | |
|---|---|---|---|
| 3,028,751 | 4/1962 | Joy | 73/634 |
| 3,251,220 | 5/1966 | Joy | 73/614 |
| 3,257,843 | 6/1966 | Cowan | 73/639 |
| 3,415,110 | 12/1968 | Cowan | 73/628 |
| 3,628,375 | 12/1971 | Pagano | 73/639 |
| 3,768,306 | 10/1973 | Stearns | 73/625 |
| 3,937,068 | 2/1976 | Joy | 73/636 |

OTHER PUBLICATIONS

Pagano et al., Detectability Evaluation of AAR-Magnetic and Dapco-Ultrasonic Rail Inspection Systems, Jul. 1976.

*Primary Examiner*—Stephen A. Kreitman
*Attorney, Agent, or Firm*—St. Onge, Steward, Johnston, Reens and Noe

[57] ABSTRACT

A system and method for performing ultrasonic inspection of a length of test material with ultrasonic transducing means emitting a beam of ultrasonic energy from within sealed wheel means containing a coupling fluid therein and having a flexible cylindrical surface member transparent to the ultrasonic beam and arranged for rolling contact along the test material. The system and method are characterized by spaced leading and trailing wheel means arranged for rolling contact along the length of test material. Ultrasonic transducer means in each of the leading and trailing wheel means are oriented so that a beam of ultrasonic energy emitted from the transducer means in one wheel means will enter the test material, be reflected from the bottom surface thereof, and be directed to and received by the transducer mean in the other wheel means. Each wheel means further includes ultrasonic transducers emitting ultrasonic energy longitudinally in front of and behind the two wheels, and side-looking transducer means for emitting ultrasonic energy into the test material transversely to the direction of travel. Additional transducers emit radiation perpendicularly through the test material. Accordingly, the test material is fully probed and many different kinds of defects can be detected. The transducers are positioned away from the test material by a distance which is substantially the near field distance of the ultrasonic beam. Means are provided for adjusting the spacing between two wheels, to allow different thicknesses of test material to be tested by interwheel transmission of the ultrasonic beam.

6 Claims, 8 Drawing Figures

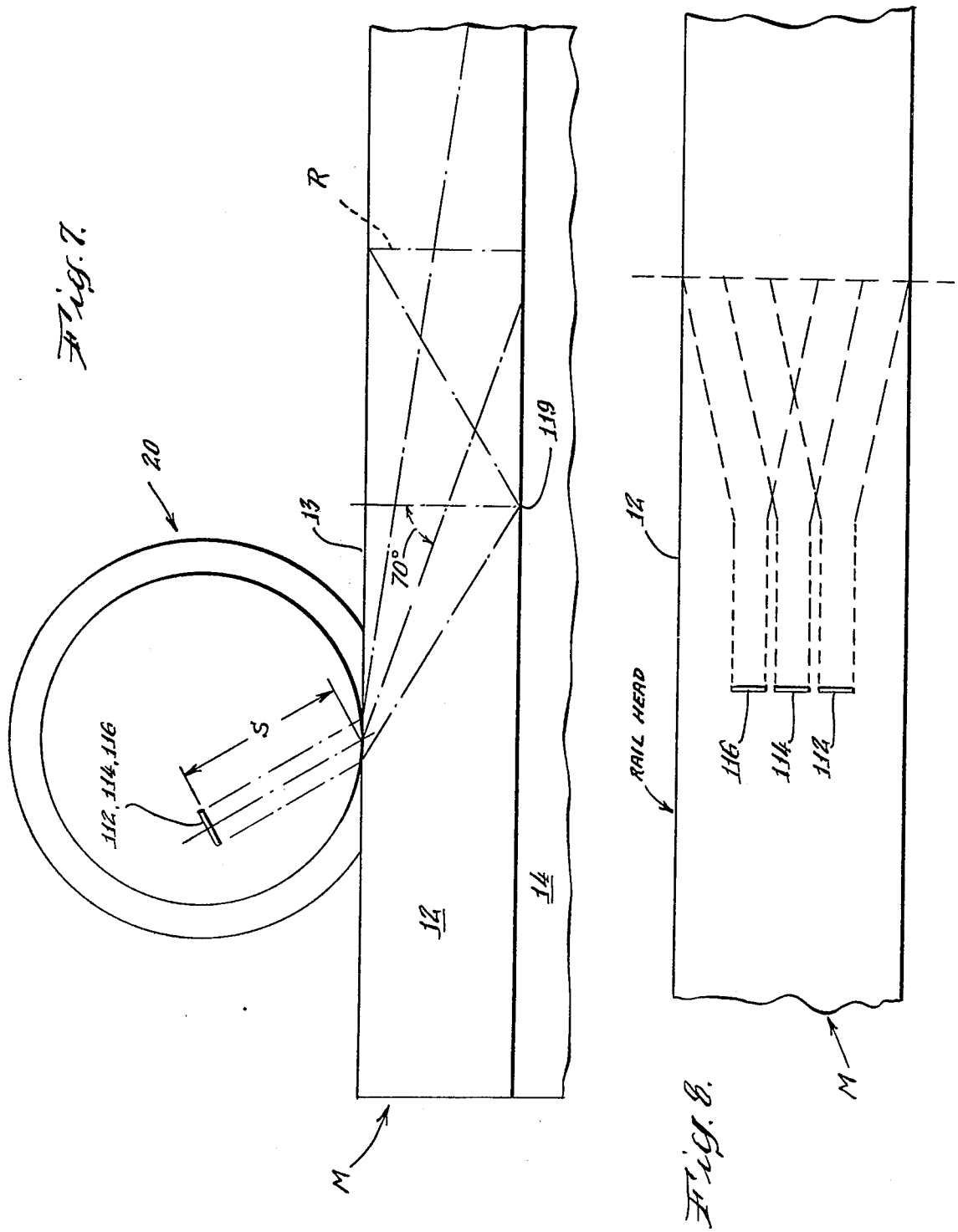

TWO WHEEL ULTRASONIC RAIL TESTING SYSTEM AND METHOD

This application is a continuation-in-part of application Ser. No. 818,544 filed July 25, 1977 for a "TWO WHEEL ULTRASONIC RAIL TESTING SYSTEM AND METHOD".

BACKGROUND OF THE INVENTION

1. Field of the Invention

This invention relates to systems and methods for the ultrasonic inspection of a length of test material such as a railroad rail and, more specifically, to ultrasonic inspection performed with ultrasonic transducing means emitting a beam of ultrasonic energy from within sealed wheel means containing a coupling fluid therein and having a flexible cylindrical surface member transparent to the ultrasonic beam and arranged for rolling contact along the test material.

2. Description of the Prior Art

Various ultransonic inspection units are known to the art for rolling contact with a length of material to be tested. One particularly advantageous example of an ultransonic testing apparatus, disclosed in my U.S. Pat. No. 3,628,375, has enabled rail testing to be performed rapidly and with more reliable detection of defects. Despite this advance, however, still more enhanced performance is desirable to detect a wider variety of defects and smaller defects.

SUMMARY OF THE INVENTION

A principal object of the present invention is to provide an improved system and method for performing ultrasonic inspection of a length of test material. A particular object of the invention is to provide such a system and method which are more sensitive to defects in the test material, are capable of detecting a wider variety of defects, and which are adaptable easily to a number of different test materials, such as different sizes of rails. Still another object of the invention is to provide a system and method for ultrasonic inspection which are more suitable for commercial use.

In a particular embodiment of the invention to be described hereinbelow in detail, the system and method are of the type for performing ultrasonic inspection of a length of test material, such as a rail, with ultrasonic transducing means emitting a beam of ultrasonic energy from within sealed wheel means containing a coupling fluid therein and having a flexible cylindrical surface member transparent to the ultrasonic beam and arranged for rolling contact along the test material. In accordance with the invention, leading and trailing wheel means are arranged for rolling contact along the length of test material. In each of the leading and trailing wheel means, ultrasonic transducer means are oriented so that a beam of ultrasonic energy emitted from the transducer means in one wheel means will enter the test material, be reflected from the bottom surface thereof, and be directed to and received by the transducer means in the other wheels means. A reading of the transmitted energy will indicate whether energy has been deflected away from the receiving transducer by defects in the test material. In more detailed aspects of the invention, the interwheel transducer means are arranged to alternately transmit and receive. The spacing between the leading and trailing wheel means is adjusted to permit ultrasonic energy to be beamed from one wheel to another through different thicknesses of test material. In addition, the interwheel transducers are positioned so that the ultrasonic beam makes a transition from the near field mode to the far field mode where it enters the test material.

In other aspects of the invention, the leading and trailing wheel means are also provided with longitudinallylooking transducer means for emitting a beam of ultrasonic energy into the test material in advance of and behind the moving wheel means, e.g., at an angle of 70° to a perpendicular to the test material surface. In addition, side-looking transducer means emit ultrasonic radiation transversely to the direction of wheel travel, e.g., with the leading wheel emitting radiation to one side, and the trailing wheel emitting radiation to the other side. Further transducers in each wheel means emit radiation perpendicularly to the test material. In one preferred embodiment of the invention, the spacing between the leading and trailing wheel means is adjusted in response to a thickness measurement of the test material taken with a transducer emitting an ultrasonic beam perpendicularly through the test material.

In still other aspects of the invention, each wheel means is provided with circular flange means internally of the flexible cylindrical surface member and carrying resilient O-rings on their outer periphery to engage the test material through the flexible cylindrical surface member and thereby accurately space the transducer means from the test material. The flexible cylindrical cover, which fits around the exterior of the flange means and is secured thereto, is free to conform to the surface of the test material and provides a large contact area for coupling of the various ultrasonic beams into the test material.

Other objects, aspects and advantages of the invention will be pointed out in, or apparent from, the detailed description hereinbelow, considered together with the following drawings.

DESCRIPTION OF THE DRAWINGS

FIG. 7 is a diagrammatic side view showing the coverage of the longitudinally-looking ultrasonic beam; and FIG. 8 is a diagramatic plan view showing the coverage of the longitudinally-looking ultrasonic beam.

DESCRIPTION OF THE PREFERRED EMBODIMENT

Figure 1:
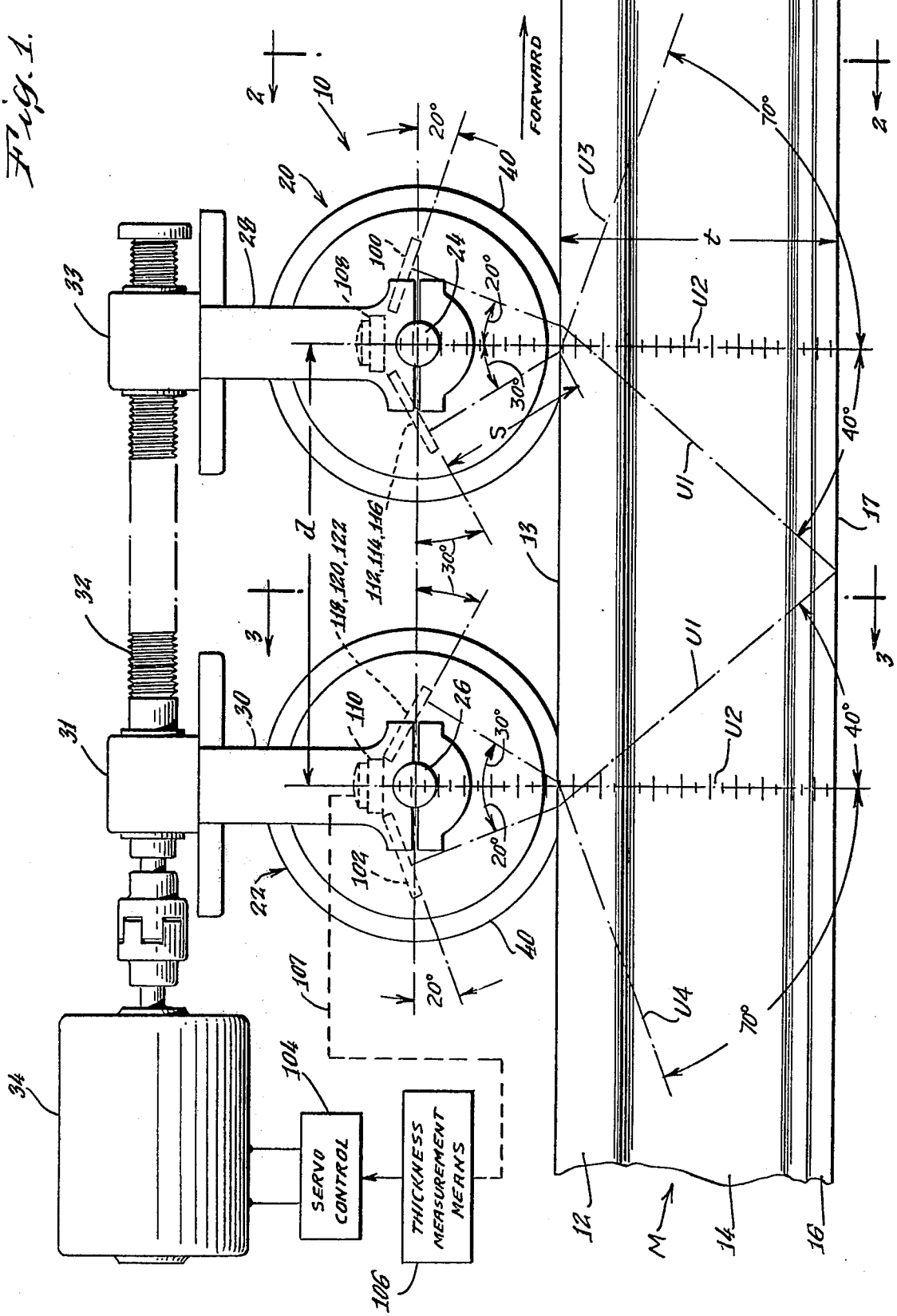
FIG. 1 is a side elevational view of an ultrasonic inspection system in accordance with the present invention.

FIGS. 1 through 5 illustrate a two wheel ultrasonic inspection system 10 arranged to detect flaws and defects in a length of test material M, illustrated as a rail having a substantially rectangular head 12 with an upper surface 13, a vertical web 14, and a base 16 with a bottom surface 17 typically resting on ties (not shown).

Arranged for rolling contact along the upper surface 13 of rail head 12 are a leading test wheel 20 and a trailing test wheel 22 separated by a distance d. The wheels 20 and 22 rotate about fixed shafts 24 and 26 secured respectively to support arms 28 and 30 which are spring loaded downward by conventional means upon a carriage (not shown) which propels the wheels along the length of test material M. As shown in FIG. 1, the support arms 28 and 30 are interconnected by means of a lead screw 32 journaled into bearing means 31 in support arm 30 and threadably engaging a screw threaded socket 33 in support arm 28 and rotated by a motor 34 to adjust the spacing distance d between the leading wheel 20 and trailing wheel 22.

Figure 2:
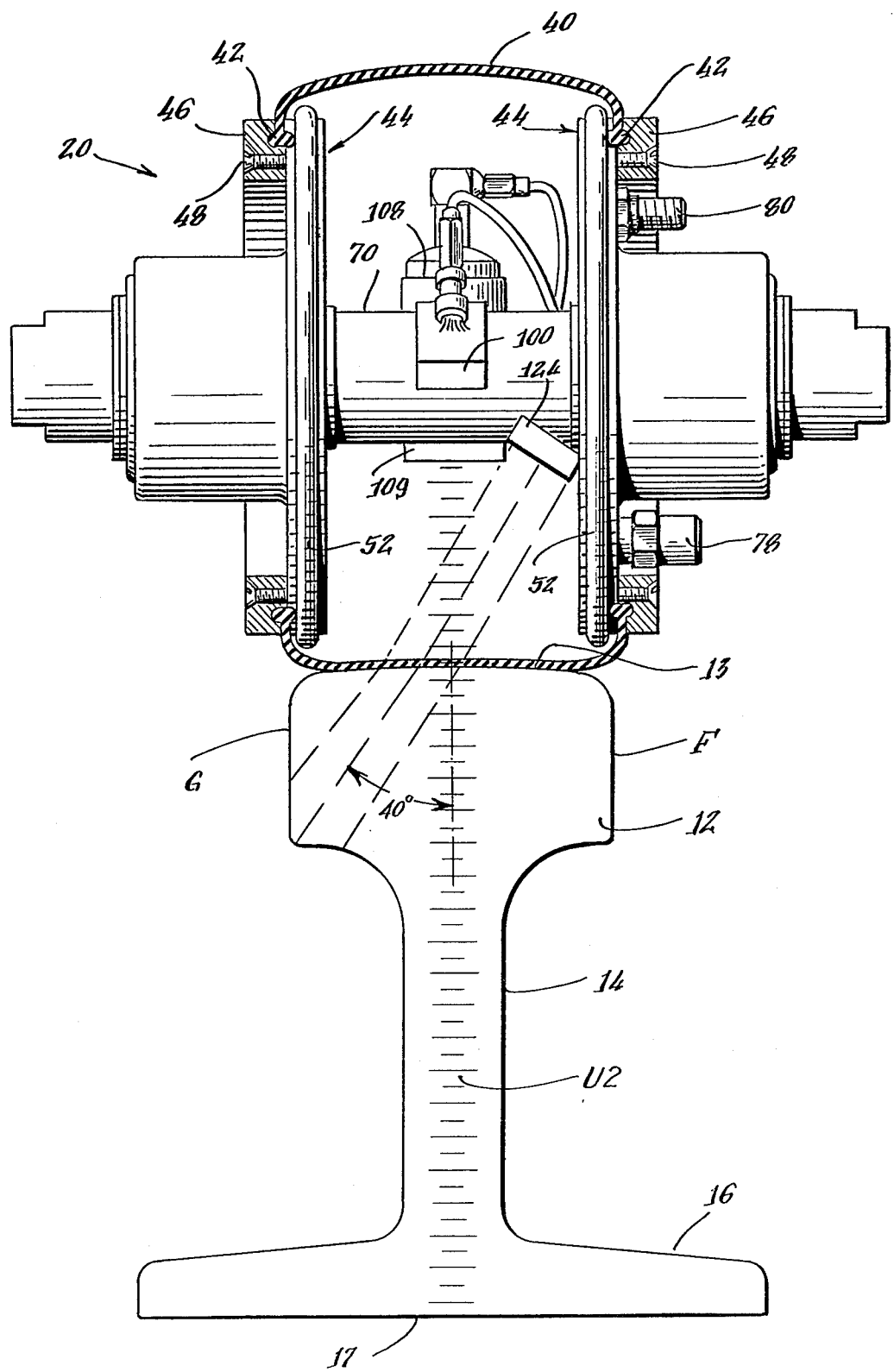
FIG. 2 is a section on line 2—2 of FIG. 1.
Figure 3:
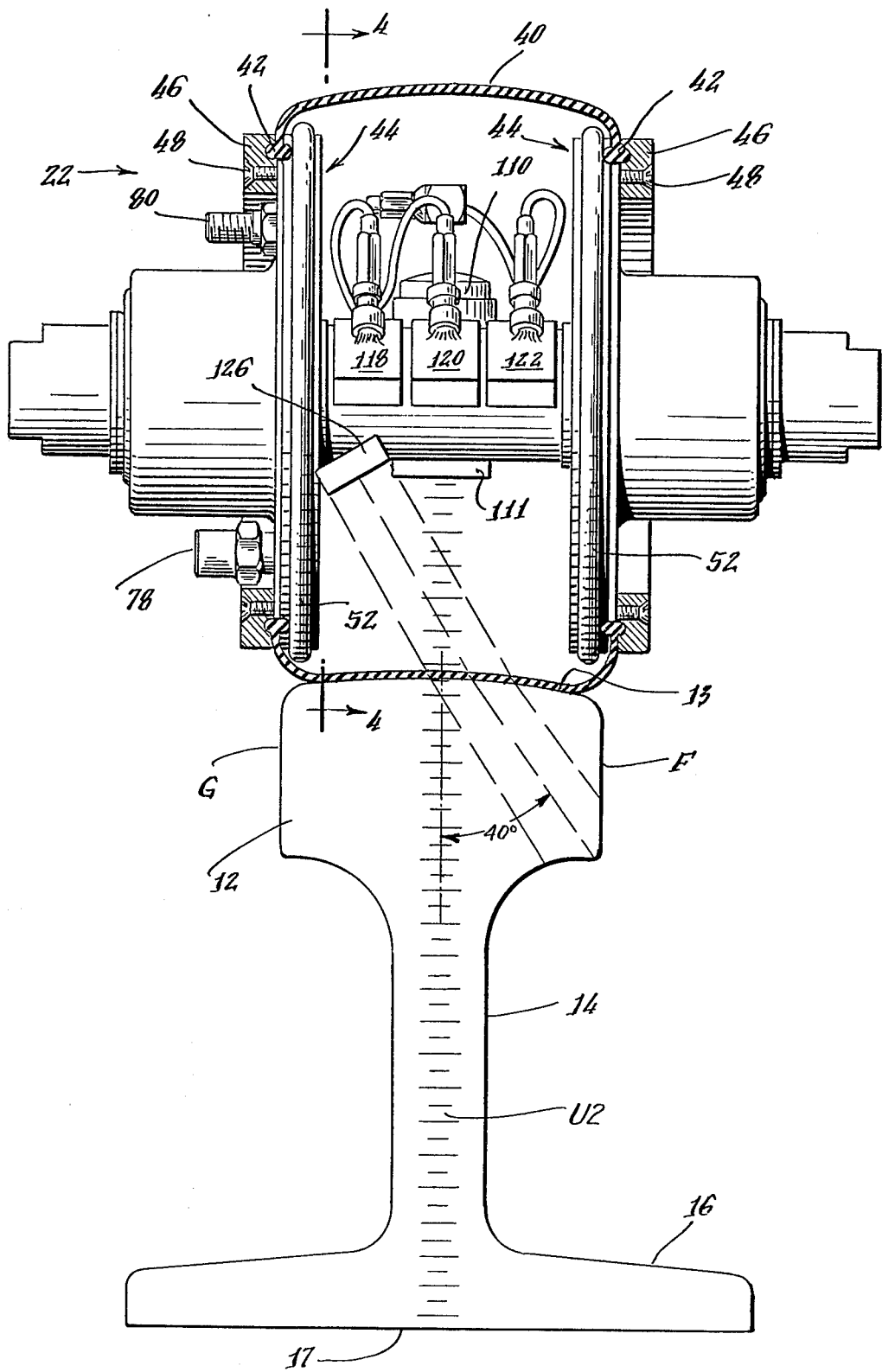
FIG. 3 is a section on line 3—3 of FIG. 1.
Figure 4:
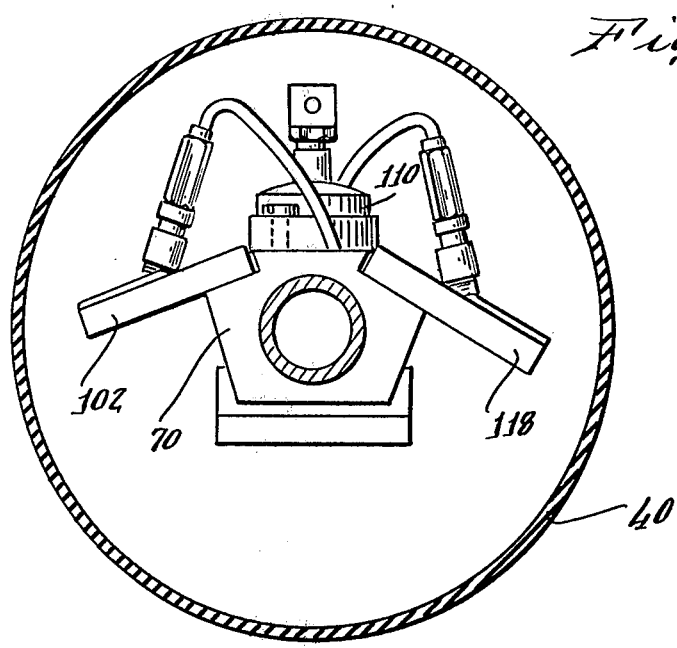
FIG. 4 is a section on line 4—4 of FIG. 3.
Figure 5:
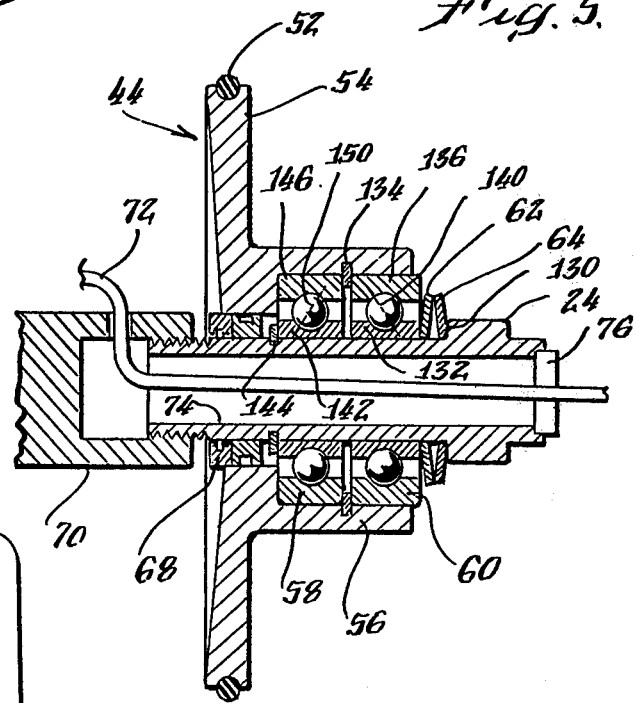
FIG. 5 is a radial section of a flange arrangement according to the invention.

As shown in FIGS. 2 and 3, the leading wheel 20 and trailing wheel 22 are each constructed with a flexible cylindrical surface member 40 made, for example, from a high durometer urethane membrane, which is transparent both visually and ultrasonically. The cylinder surface member 40 is provided with outer beads 42 which are clamped in opposed circular grooves in flange members 44 and clamping rings 46 secured to the flange members by screws 48. The flange members 44, as shown in FIG. 5, have a circular peripheral groove 50 seating a circumferential rubber O-ring 52. The O-ring 52, which is located internally of the cylindrical surface member 40, is arranged to press down on the upper surface 13 of the test material M through the flexible member 40 (FIGS. 2 and 3) to accurately space the axes of wheels 20 and 22 from the upper surface 13 of the test material M. As will be explained below, this provides predetermined path distances for ultrasonic beams emitted by transducers mounted within the wheels, and improves inspection capabilities. In FIGS. 2 and 3, for purpose of illustration, the rings 52 are shown slightly away from pressing the flexible member 40 down fully onto surface 13.

As shown in FIG. 5, the flange member 44 comprises a disc portion 54 integral with a hub portion 56 which is rotatably connected to one of the fixed shafts 24 (or 26) by means of preloaded double bearings 58 and 60 with spring pressure applied axially thereto through opposed Bellville washers 62 and 64. A fluid seal between fixed shaft 24 and flange member 44 is achieved with a magnetic seal 68, such as that commercially available from Magnetic Seal Corporation, West Barrington, Rhode Island. At its inner end, fixed shaft 24 threadably engages a transducer mounting yoke 70 which carries ultrasonic transducers in a manner to be described below. Signal cables 72 for the ultrasonic transducers are led externally of the testing wheels 20 and 22 through a bore 74 in shaft 24 and through a fluid seal 76. As shown in FIGS. 2 and 3, fluid fill and air bleed check valves 78 and 80 are provided in the disc portions 54 of flange members 44. The sealed interior portions of leading wheel 20 and trailing wheel 22 are filled with an ultrasonic coupling fluid, composed for example of water, glycol, or a mixture thereof such as 40% glycol and 60% water.

As illustrated in FIG. 1, the mounting yoke 70 of the leading wheel 20 carries a rearward-looking ultrasonic transducer 100 which is oriented to emit a beam of ultrasonic energy U1 (shown by a dashed line) which travels through the coupling fluid within wheel 20 and through the flattened region where cylindrical surface 40 contacts the upper surface 13 of test material M. This transducer 100 may preferably be a crystal transducer having an active area ½ of an inch wide and ¾ of an inch long as measured along its inclined direction, as seen in FIG. 1.

The beam of ultrasonic energy is refracted in accordance with Snell's law due to the different propagation velocities of the beam in the wheel fluid and in the steel rail, and travels to the bottom surface 17 of the test material M where it is reflected upwardly and travels through the rail to the flattened region of the other wheel membrane where the cylindrical surface 40 of trailing wheel 22 contacts the test member. The beam is then again refracted into the coupling fluid within the trailing wheel 22 to a forward-looking transducer 102 carried by the mounting yoke 70 in trailing wheel 22.

Transducers 100 and 102 are similar in size and construction but are aimed backward and forward, respectively, relative to the direction of travel of the inspection system. These two transducer 100 and 102 are mounted to be aimed at the same angle to the perpendicular to surface 13, e.g. 20°, to provide a symmetrical propagation path for the ultrasonic beam U1. The two transducers are each used in turn as a sender and a receiver, and preferably their roles are switched every cycle, i.e. the transmitter becomes the receiver and vice versa on alternate cycles. The received signal amplitude is monitored and if any defects lie in the path of the ultrasonic beam in the test material, a corresponding drop in amplitude would be detected. This arrangement is ideally suited for the inspection of welds in welded rails since the response is dependent less on defect orientation than on defect size. The transducers 100 and 102 are oriented with respect to the perpendicular to provide an ultrasonic beam which is emitted into the test material at a resultant angle of about 40° to the perpendicular to surface 13. To provide this resultant angle in a test material of steel from a wheel filled with a mixture of 60% water and 40% ethylene glycol, the transducers 100 and 102 are each oriented to transmit a beam in the liquid at an angle of about 20° to the perpendicular to the rail surface 13. The liquid may contain corrosion inhibitors. Other anti-freeze solutions may be used, such as pure ethylene glycol, in which event the velocity of sound propagation in the liquid may be somewhat different from the present example, and thus the particular angles at which the transducers are aimed are slightly changed. Also, changes in temperature slightly change the propagation velocities and angular relationships.

It will be observed that the orientation angle of transducers 100 and 102 is dependent upon the spacing distance d between the leading and trailing wheels 20 and 22 and the thickness t of the test material. This adjustment is desirable since the height of a railroad rail is proportionate to its weight. It is not uncommon for railroads to have several tracks incorporating varying heights. For example, a main line rail may weigh approximately 125 pounds per yard of length, a heavy traffic line rail may weigh approximately 140 pounds per yard of length, and a spur line track may weigh approximately 72 pounds per yard of length, and other weights and sizes of rail are also used.

So that the transducers may be fixedly mounted to yokes 70, and so that substantially a 40° propagation angle in the test material may be maintained for different thicknesses "t" of test material, motor 34 is operated to cause lead screw 32 to adjust the spacing d between the wheels. Preferably, the spacing d is adjusted automatically through a servo-control 104 for the motor 34 which responds to a thickness measuring means 106. This thickness monitoring means as shown by the dashed connection line 107 serves to monitor one of the so-called "zero degree" transducers 110, as shown (or 108, if desired). These zero degree transducers 110 and 108 are aimed virtually straight down, and thus the time required for the vertical ultrasonic beam U2 to travel down through the rail being tested and to be reflected from the bottom surface 17 and to travel back up to the top surface 13 indicates the exact height of the rail. The thickness measurement means 106 measures this rail height "t", and the servo control 104 then automatically adjusts the spacing "d" in accordance with the height of the rail line being tested.

It is preferred that the mode of vibration utilized for testing in the steel rail be the shear wave mode. There is longitudinal sound wave transmission and shear wave sound transmission in steel. The longitudinal is a much faster sound transmission mode having a velocity of approximately 5,900 meters per second and thus has a longer wavelength. This longer wavelength provides less resolution in searching for rail defects. Conversely, the shear wave (also called transverse wave) mode is slower transmission velocity of about 3,200 meters per second and thus has a resultant shorter wavelength. Therefore, the shear wave mode provides a greater resolution so as to enable smaller defects in the rail to be found. It is to be noted that when the shear wave beam is refracted to be travelling at an angle of approximately 35° or more to the perpendicular, then the longitudinal wave is refracted to an angle of 90° or more to be perpendicular and thus becomes a surface wave proceeding along the top surface 13 and is thereby dissipated. It is to be noted that the liquid within the wheels 20 and 22 is not capable of supporting a shear wave mode of sound transmission. Thus, there occurs a mode conversion from longitudinal to shear wave as the ultransonic vibrational energy enters the rail from the liquid and there is the reverse mode conversion from shear wave to longitudinal wave as the ultrasonic vibrational energy enters the liquid from the rail.

Generally speaking, it is not desirable to use an angle much larger than 70° within the steel rail, because more than 70° unduly magnifies the effect of changes in velocity in the liquid upon changes in the angle of beam direction in the steel.

Preferably, the leading and trailing wheels 20 and 22 have zero degree transducers 108 and 110 which are oriented to emit beams U2 of ultrasonic energy downward perpendicularly through Teflon (polytetrafluoroethylene) waveguides 109 and 111 (FIGS. 2 and 3) to surface 13 into the test material. The downward-looking (zero degree) transducers 108 and 110, used in a pulse echo mode, can indicate whether there is a head and web separation, and can indicate the presence of bolt holes, bolt hole cracks, and some vertical split heads that occur in the web region. It is to be noted that these zero degree transducers 108 and 110 are mounted high up within the wheel. This location advantageously provides a long travel path of at least two inches within the wheel, which avoids problems of undesired echoes interfering with the reflected energy U2 returning from the bottom 17 of the test material M. The Teflon waveguides 109 and 111 serve to reduce beam divergence and thus also eliminate false echoes. In addition, by monitoring the time it takes for ultrasonic energy to be transmitted to the bottom surface 17 of the test material and reflected back to the transducer 108 or 110, as mentioned above, a measurement of thickness can be obtained and, therefore, as shown in FIG. 1, the ultrasonic transducer such as 110 may be used to supply a signal to the thickness measurement means 106.

The leading wheel 20 further carries an array of three horizontally spaced transducers 112, 114 and 116 oriented to send a beam of ultrasonic energy U3 fowardly into the length of test material M and substantially longitudinally therein, e.g. at a resultant angle of 70° to the perpendicular to the upper surface 13 of the test material. To provide a resultant angle of 70° in steel, from a 60% water-40% glycol mixture, the transducers 112, 114 and 116 are oriented to emit a beam at an angle of about 28° to 30° to the perpendicular. In a similar manner, trailing wheel 22 is provided with a horizontally spaced array of three transducers 118, 120 and 122 oriented to send a beam U4 of ultrasonic energy in a rearward direction at a resultant angle of about 70° to the perpendicular. One particular arrangement for the arrays of ultrasonic transducers 112, 114 and 116 and 118, 120, 122 which is very useful for rail testing comprises active elements with face dimensions of $\frac{1}{2}$" diameter spaced by a center-to-center distance of $\frac{5}{8}$". By spacing the transducers so that the emit the beam through a path distance s from the upper surface 13 of the test material with s being substantially the near field distance N of the ultrasonic beam, as calculated using standard formulas, then the diverging ultrasonic beam from the array of transducers provides substantially 100% lateral coverage of the rail head 12 at a distance of about 3" in front of the wheel (FIGS. 7 and 8).

As shown in FIG. 7, the diverging beam fills the entire cross-sectional area of the rail head in the region R at a distance of about 6 inches from the location of the bottom of the test wheel. This occurs by virtue of the reflection at 119 from the lower surface of the rail head.

In effect, by utilizing three transducers each having a small active area of about 0.20 square inches, i.e. approximately 12.7 mm in diameter, the near and far field effects are being manipulated. The result is to provide a shorter near field which terminates near the refracting interface contact surface at the bottom of the wheel. Thus, a greater divergence of the far field is produced within the rail head. Accordingly, transverse defects that occur anywhere within the head area can be detected. As a typical example, the near field distance N of a beam of ultrasonic energy of a frequency of 2.25 Megahertz in a mixture of 60% water and 40% ethyl glycol is about 2.16 inches, as calculated according to the formula $$N = 0.25 (D^2 f/c)$$

where

D = diameter = 12.7 mm. of the active surface of the transducer f = sound frequency = $2.25 \times 10^6$ c = second velocity = 1675 meters per second at room temperature As shown in FIG. 1, the transducers 100, 102, 108 and 110 are spaced along their emission paths from the refracting interface at the surface 13 of test material M by a distance which is substantially the near field distance of the ultrasonic beams emitted therefrom. This provides good coverage by the ultrasonic beams and accurate inspection of the test material.

Figure 6:
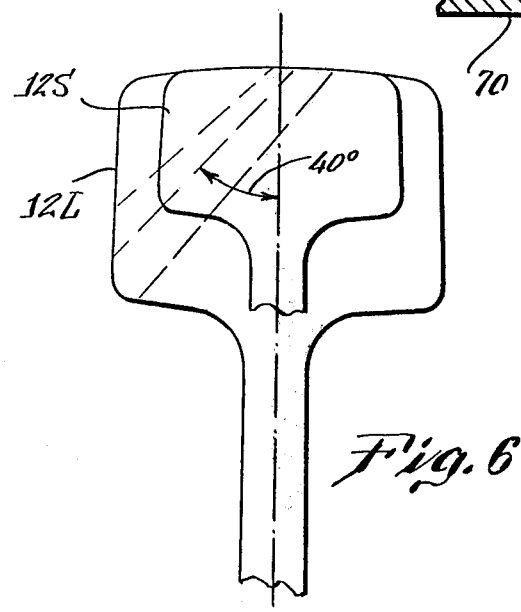
FIG. 6 is a sectional view through different superimposed rail sections showing the coverage of the side-looking ultrasonic beam.

In addition, the mounting yoke 70 of the leading wheel 20 carries a side-looking transducer 124 which emits a beam of ultrasonic energy toward the lower corner of the rail head 12 on the gauge side G of the rail, and trailing wheel 22 carries a side-looking transducer 126 which emits a beam of radiation toward the lower corner of the rail head 12 on the opposite or field side of the rail. The side-looking transducers 124 and 126 are oriented to emit a beam of ultrasonic energy into the test material at a resultant angle of about 40° to the perpendicular. Such an angle, as shown in FIG. 6, will be directed to the lower corner of a small rail head 12S and also to the lower corner of a large rail head 12L. As standard rails vary from 72 pounds per yard in weight to 140 pounds per yard in weight, with cross sections increasing accordingly, the testing system is able to accommodate all expected rail sizes. The side-looking transducers 124 and 126 are monitored for loss of amplitude of the reflection received back from the lower corner of the rail head. This indicates the presence of any vertical split head defect (which is a defect oriented parallel to the gauge and field side and would run longitudinally down the rail) which is a defect not heretofore reliably detected using ultrasonics.

By incorporation of a two-wheel test system 10 of twelve individually monitored transducers oriented as described above, the rail is essentially completely probed for the various kinds of defects that could lead to failures and possible derailments. This is accomplished by the sole use of ultrasonic energy, thereby eliminating the need of any supplementary equipment, such as magnetic induction systems which have traditionally limited testing speeds to a maximum of 8 miles per hour. The ultrasonic two-wheel inspection system 10, as described above, will allow testing in excess of 30 miles per hour thereby substantially reducing inspection costs per mile.

Inviting attention again to FIG. 5, it is noted that the spring washers 62, 64 push inwardly against a shoulder 130 on the axle 24 and push outwardly against the inner race 132 of the inner ball bearing 60. Then a snap ring 134 in a groove in the hub portion 56 anchors the outer race 136 of the inner ball bearing 60. The result is to tend to push the inner race 132 inward (to the left) while the outer race 136 relatively is pushed to the right. This pre-loading of the bearing 60 creates a canted line of action 140 of pressure on each of the balls. Conversely, the other bearing 58 has its inner race 142 held by a snap ring 144 in a groove in the axle 24 while its outer race is held by the other snap ring 134. The resultant pre-loading on the bearing 58 is thus in the opposite relative sense such that the line of action 150 of pressure on each of the balls is canted in the opposite direction. The relatively opposed sense of pre-loading of the respective races of a pair of bearings located side-by-side on the axle is advantageous in saving wear and tear. The vibration, wabble, or slap of the bearings, is prevented because they are each pre-loaded in a predetermined sense. There is no opportunity for the balls to "hunt" as they roll around in their races. They are forced to track true. The result in actual practice is to give a significantly increased operating life and to allow these relatively small diameter wheels to roll along precisely without bearing vibration up to 30 miles per hour or more.

Although a specific embodiment of the invention has been disclosed herein in detail, it is to be understood that this is for the purpose of illustrating the invention and should not be construed as necessarily limiting the scope of the invention since it is apparent that many changes can be made to the disclosed structures by those skilled in the art to suit particular applications.

ADDENDUM

As described above, the utilization of the downwardly-rearwardly aimed transducer 100 in the leading wheel means 20 plus the downwardly-forwardly aimed transducer 102 in the trailing wheel means 22 is ideally suited for inspection of welds in welded rails since the response is dependent less on defect orientation than on defect size. For example, in such welds, it is possible that there may be a generally planar crack or lack of bonding oriented in the vertical plane, i.e. perpendicular to the side and top rail surface 13. Such a vertical plane defect is often difficult to detect by the zero degree transducers 108 and 110 with their vertical beams U2 because of the small reflecting cross section of such a defect as seen looking straight down, in effect, the transducers 108 and 110 are only looking at the edge of such a defect. Also, such a vertical plane defect is often difficult to detect by the side-looking transducers 124 and 126 for similar reasons. In summary, a vertical plane defect even though tending to be highly reflective of an ultrasonic energy beam presents only a small percentage of its actual area as seen looking down (beams U2) or as seen in the direction of the side-looking transducers 124 and 126.

Moreover, such a vertical plane defect is often difficult to detect by the arrays of transducers 112, 114, 116, 118, 120 and 122 transmitting the beams U3 and U4 at an angle of approximately 70° to the perpendicular because the orientation of the effective vertical plane of such a defect tends to reflect the energy downwardly and away from the respective tranducer array.

However, such a vertical plane defect is very effectively intercepted by the beam U at an angle of approximately 40° to the perpendicular produced by the transducers 100 and 102 and being reflected off of the bottom surface 17 of the rail. Such vertical plane defect tends to block the transmitted beam of energy from reaching the receiving transducer, thereby readily revealing its presence by producing a drop in amplitude of the received signal as described above. It is to be understood that the beam U1 at an angle of approximately 40° to the perpendicular travels down at this angle to the bottom 17 of the rail and is reflected therefrom, thereby generally inspecting the rail from top to bottom.

It is to be noted that vertical plane defects, sometimes called transverse defects, can also develop in the head area of a railroad rail at regions other than a weld as a result of stressing.

In addition to vertical plane defects, there may also be irregularly oriented defects caused by slag inclusions or porosity in the weld regions. Such irregularly shaped defects, even though they may be relatively large, do not tend to reflect much energy in any given direction, i.e. they tend to produce a scattering effect on the ultrasonic beam. Therefore, such energy-scattering defects may also be difficult to detect by the zero degree transducers 108 and 110 and by the side-looking transducers 124 and 126 and by the arrays 112, 114, 116 and 118, 120 and 122.

These energy-scattering type defects are readily detected by the resultant blocking or shadowing effect produced on the beam U1, thereby producing a drop in amplitude of the received signal.

As described above, the two transducers 100 and 102 are each used in turn as a sender and a receiver, and preferably their roles are switched every cycle, i.e. the transmitter becomes the receiver and vice versa on alternate cycles. By virtue of alternating the send-receiver sequence the particular transducer which is serving as the transmitter can also be used as a receiver immediately after the pulse transmission has ceased, thus listening for echoes (i.e. reflected energy). In this method where a reflective (echo) mode is being used together with a through-transmission (blocking or shadowing) mode, the bolt hole region of jointed rails (i.e. non-welded rail) can be inspected for bolt hole cracks. This inspection is thus being made in alternate directions on each successive cycle.

The reason why it is desirable to inspect jointed rail alternately in opposite directions by such a combined method of reflective mode plus through-transmission mode is that the vertical joint (or air space) between the adjacent rail ends blocks the through-transmission mode as soon as the leading wheel has crossed over the joint and the joint also blocks the reflective energy from reaching the end portion of the adjacent rail where certain of the bolt holes are located. Therefore, by utilizing both reflective and through-transmission modes and by alternating their directions on successive cycles a very effective inspection method is provided in spite of the difficulties caused by the inherent massive discontinuity presented by the joint itself between rail ends.

In summary, the system and method of the present invention provide very effective inspection of welded rail and also of jointed rail, whichever may be encountered in travelling along a railroad to be inspected.

I claim:

1. In a system of the type for performing ultrasonic inspection of a length of test material, such as a rail, with ultrasonic transducing means emitting a beam of ultrasonic energy from within sealed wheel means containing a coupling liquid therein and having a flexible membrane transparent to the ultrasonic beam and arranged for rolling contact along the test material, rail inspection apparatus comprising:
   leading wheel means arranged for rolling contact along the length of rail,
   trailing wheel means spaced behind the leading wheel means and arranged for rolling contact along the length of rail,
   first ultrasonic transducer means mounted in the leading wheel means aimed at an angle downwardly and rearwardly and second ultrasonic transducer means mounted in the trailing wheel means aimed at an angle downwardly and forwardly for transmitting ultrasonic energy from one of said transducer means to the other longitudinally through the rail at an angle to the top surface thereof,
   third ultrasonic transducer means mounted in one of said wheel means aimed at an angle downwardly and laterally for transmitting ultrasonic energy in the rail in a side-looking direction substantially perpendicularly to the side surface of the rail and at a resultant angle of approximately 40° to the perpendicular to the top surface of the rail toward the lower gage corner of the rail head and for obtaining optimum reflection of ultrasonic energy from the lower gage corner, regardless of the various sizes of rail heads encountered, to detect loss of amplitude of the energy caused by impingement with a defect,
   fourth ultrasonic transducer means mounted in the other wheel means aimed at an angle downwardly and laterally for transmitting ultrasonic energy in the rail in a side-looking direction substantially perpendicularly to the side surface of the rail and at a resultant angle of approximately 40° to the perpendicular to the top surface of the rail toward the lower field corner of the rail head and for obtaining optimum reflection of ultrasonic energy from the lower field corner, regardless of the various sizes of the rail heads encountered, to detect loss of amplitude of the energy caused by impingement with a defect, and
   fifth ultrasonic transducer means in at least one of said wheel means aimed downwardly at a zero angle to the perpendicular to the top surface of the rail,
   thereby effectively probing the rail for various kinds and orientations of defects regardless of whether the rail is welded or jointed.

2. In a method for performing ultrasonic inspection of a length of test material, such as a rail, with ultrasonic transducing means emitting a beam of ultrasonic energy from within sealed wheel means containing a coupling liquid therein and having a membrane transparent to the ultrasonic beam and arranged for rolling contact along the test material, the rail inspection method comprising the steps of:
   providing leading and trailing wheel means,
   providing first ultrasonic transducer means in said leading wheel means mounted in a fixed location relative to the axis thereof aimed at an angle downwardly and rearwardly and providing second ultrasonic transducer means in said trailing wheel means mounted in a fixed location relative to the axis thereof aimed at an angle downwardly and forwardly for directing ultrasonic energy in a beam from one of said transducer means to the other in the through-transmission mode wherein the beam of energy travels from one at an angle downwardly and longitudinally within the rail for reflection from the bottom of the rail to travel upwardly and longitudinally within the rail to be received by the other,
   providing means for changing the longitudinal spacing between said leading and trailing wheel means,
   providing third ultrasonic transducer means within one of said wheel means aimed downwardly perpendicular to the top surface of the rail,
   sensing the time required for ultrasonic energy from the third transducer means to travel down through the rail to be reflected from the bottom surface and to travel back to the third transducer means, to sense the height of the rail along which said wheel means are rolling, and
   automatically and continuously changing the longitudinal spacing between said wheel means in response to changes in rail height for compensating for such changes to maintain the first and second transducer means in alignment with the beam of energy to be transmitted and received between them.

3. The rail inspection method as claimed in claim 2 further comprising the steps of:
   utilizing each of said transducer means in turn as a transmitter and as a receiver in predetermined sequence, and
   also utilizing the transmitter as a receiver for operation in the reflection mode.

4. The rail inspection method as claimed in claim 3, wherein said predetermined sequence comprises alternating the roles of transmitter and receiver in each successive cycle.

5. In a method for performing ultrasonic inspection of a length of test material, such as a rail, with ultrasonic transducing means emitting a beam of ultrasonic energy from within sealed wheel means containing a coupling liquid therein and having a membrane transparent to the ultrasonic beam and arranged for rolling contact along the test material, the rail inspection method comprising the steps of:

providing leading and trailing wheel means, providing first and second ultrasonic transducer means in the respective wheel means aimed laterally downwardly toward opposite lower corners of the rail head substantially perpendicularly to the side surface thereof, transmitting ultrasonic energy from the first transducer means for reflection from the one lower corner of the rail head toward which it is aimed and receiving the reflected energy therefrom to detect loss of amplitude of energy caused by impingement with a defect, and transmitting ultrasonic energy from the second transducer means for reflection from the other lower corner of the rail head toward which it is aimed and receiving the reflected energy therefrom to detect loss of amplitude of energy caused by impingement with a defect, said ultrasonic energy further being transmitted in the rail head from each of said first and said second transducer means at a resultant angle of approximately 40° to the perpendicular to the top surface of the rail for obtaining optimum reflection of ultrasonic energy from the lower corner of the rail head toward which each of said first and second transducer means is respectively aimed regardless of various sizes in rail heads encountered.

6. In a system of the type for performing ultrasonic inspection of a length of test material, such as a rail, with ultrasonic transducing means emitting a beam of ultrasonic energy from within sealed wheel means containing a coupling liquid therein and having a flexible membrane transparent to the ultrasonic beam and arranged for rolling contact along the test material, rail inspection apparatus which comprises:

leading wheel means arranged for rolling contact along the length of rail, trailing wheel means spaced behind said leading wheel means and arranged for rolling contact along the length of rail, first ultrasonic transducer means mounted in said leading wheel means aimed laterally downwardly toward the lower gage corner of the rail head for transmitting a beam of ultrasonic energy in the rail in a side-looking direction substantially perpendicularly to the side surface of the rail and at a resultant angle of approximately 40° to the perpendicular to the top surface of the rail and for obtaining optimum reflection of ultrasonic energy from the lower gage corner, regardless of various sizes of rail heads encountered, to detect loss of amplitude of the energy caused by impingement with a defect, and second ultrasonic transducer means mounted in said trailing wheel means aimed laterally downwardly toward the lower field corner of the rail head for transmitting a beam of ultrasonic energy in the rail in a side-looking direction substantially perpendicularly to the side surface of the rail and at a resultant angle of approximately 40° to the perpendicular to the top surface of the rail and for obtaining optimum reflection of ultrasonic energy from the lower field corner, regardless of various sizes of rail heads encountered, to detect loss of amplitude of energy caused by impingement with a defect.

* * * * *